wille et al.

United States Patent [19]

[11] Patent Number: 5,843,979
[45] Date of Patent: Dec. 1, 1998

[54] TRANSDERMAL TREATMENT WITH MAST CELL DEGRANULATING AGENTS FOR DRUG-INDUCED HYPERSENSITIVITY

[75] Inventors: John J. Wille, Trenton; Agis F. Kydonieus, Kendall Park, both of N.J.

[73] Assignee: Bristol-Myers Squibb Company, Skillman, N.J.

[21] Appl. No.: 598,627

[22] Filed: Feb. 12, 1996

Related U.S. Application Data

[63] Continuation of Ser. No. 198,003, Feb. 17, 1994, abandoned, which is a continuation-in-part of Ser. No. 22,080, Feb. 25, 1993, abandoned.

[51] Int. Cl.$^6$ .......................... A61K 31/40; A61K 31/20
[52] U.S. Cl. .......................................... 514/408; 514/558
[58] Field of Search ...................... 514/408, 558

[56] References Cited

U.S. PATENT DOCUMENTS

| | | | |
|---|---|---|---|
| 455,036 | 10/1995 | Stäb et al. | 424/401 |
| 485,154 | 12/1989 | Cormier . | |
| 500,956 | 3/1991 | Amkraut . | |
| 4,897,260 | 1/1990 | Ross . | |
| 5,028,431 | 7/1991 | Franz . | |
| 5,049,387 | 9/1991 | Amkraut . | |
| 5,077,054 | 12/1991 | Amkraut . | |
| 5,118,509 | 6/1992 | Amkraut . | |
| 5,120,545 | 6/1992 | Ledger . | |
| 5,130,139 | 7/1992 | Cormier . | |
| 5,296,225 | 3/1994 | Adekunle et al. | 424/195.1 |

FOREIGN PATENT DOCUMENTS 2229892  7/1992  Australia .

OTHER PUBLICATIONS

S. Gruner, H. Oesterwitz, H. Stoppe, W. Henke, R. Eckert, and N. Sonnichsen. Cis–Urocanic Acid as a mediator of ultraviolet light–induced immunosuppression. Seminars in Hematol. 29:(2), 102–107, 1992.

S. Gruner, W. Diezel, H. Stoppe, H. Oesterwitz and W. Henke. Inhibition of skin allograft rejection and acute graft–versus–host disease by cis–urocanic acid. J. Invest. Dermatol. 98: 459–462, 1992.

R. H. Guymer and T.E. Mandel. Urocanic acid and allotransplantation. Transplant. Proc. 22 (5) ; 2119–2120, 1990.

T.G. Harriot–Smith and W.J. Halliday. Suppression of contact hypersenitivity by short–term ultraviolet irradiation: II. The role of urocanic acid. clin. exp. Immunol. 72: 174–177, 1988.

I. Kurimoto and J. W.. Streilein. Cis–urocanic acid suppression of contact hypersenitivity induction is mediated via tumor necrosis factor–α. J Immunol. 148: 3072–3078, 1992.

I. Kurimoto and J. W. Streilein. Deleterious effects of cis–urocanic acid and UVB radiation on Langerhans cells and on induction of contact hypersensitivity are mediated by tumor necrosis factor–alpha. J. Invest. Dermatol., 99: 69S–70s, 1992.

W.L. Morison and S.P. Kelley. Urocanic acid may not be the photoreceptor for UV–induced suppression of contact hypersensitivity. Photodermatol. 3: 98–101, 1986.

A.M. Moodycliffe, I. Kimber and A.M. Norval. The effect of ultraviolert B irradiation and urocanic acid isomers on dendritic cell migration. Immunology 77: 394–399, 1992.

F.P. Noonan, E.C. De Fabo and H. Morrison. Cis–urocanic acid, a product formed by ultraviolet B irradiation of the skin, initiates and antigen presentation defect in splenic dendritic cells in vivo. J. Invest. Dermatol. 90: 92–99, 1988.

F.P. Noonan and E.C. De Fabo. Immunosuppression by ultraviolet B radiation: initiation by urocanic acid. Immunology Today 13 (7) : 250–254, 1992.

M. Norval, J. W. Gilmour and T.J. Simpson. The effect of histatmine receptor antagonists on immunosuppression indcued by the cis–isomer of urocanic acid. Phortodermatol Photoimmunol. Photomed. 7: 243–248, 1990.

M. Norval, T.J. Simpson and J.A. Ross. Urocanic acid and immunosuppression. Photochem & Photobiol., 50(2) : 267–273, 1989.

M. Norval, J.T. Simpson, E. Bardsihri and S. E. Howie. Urocanic acid analogues and the suppression of the delayed–type hypersensitivity response to Herpes simplex virus. Photochem. & Photobiol. 49(5) : 633–639, 1989.

E.W. Palaszynski, F.P. Noonan and E.C. De Fabo. Cis–urocanic acid down–regulates the induction of adenosine 3', 5'–cyclic monophosphate by either trans–urocanic acid or histamine in human dermal fibrtoblasts in vitro. Photochem. & Photobiol. 55(2) : 165–171, 1992.

L. Rasanen, C.T. Jansen, T. Reunala and H. Morrison. Stereospecific inhibition of human epidermal cell interleukin–1 secretion and HLA–DR expression by cis–urocanic acid. Photodermatol. 4: 182–186, 1987.

V. E. Reeve, G.E. Greenoak, P.J. Canfield, C. Boehm–Wilcox, and C.H. Gallagher. Topical urocanic acid enhances UV–induced tumor yield and malignacy in the hairless mouse. Photochem. & Photobiol., 49 (4) : 459–464, 1989.

(List continued on next page.)

*Primary Examiner*—Zohreh Fay
*Attorney, Agent, or Firm*—John M. Kilcoyne; Theodore R. Furman, Jr.

[57] ABSTRACT

Methods and compositions for inhibiting or preventing the skin irritating or sensitizing effects of a skin irritating or sensitizing component of a dermal or transdermal drug delivery system are disclosed. The composition comprises a mast cell degranulating agent which is capable of inducing a state of immunological tolerance to the skin sensitizing agent by delivery prior to, or at the onset of transdermal drug delivery. Such an agent, preferably cis-urocanic acid or an analogue or metabolite thereof, can be administered before, during or after each transdermal drug delivery to achieve immune tolerance countersensitization. Alternatively, the agent can be used to induce countersensitization. The agent is preferably capable of permeating the epidermis and is administered transdermally. Novel methods and compositions comprising cis-urocanic acid or an analogue or metabolite thereof to obtain anti-inflammatory effects are also disclosed.

31 Claims, 2 Drawing Sheets

OTHER PUBLICATIONS

V.E. Reeve and L.E. Mitchell. Hazards of urocanic acid as a cosmetic ingredient. Photodermatol Photoimmuno. Photomed. 8: 176–180, 1991.

V.E. Reeve, M. Bosnic and E. Rozinova. Carnosine (β–alanylhistdine) protects from the suppression of contact hypersensitivity by ultraviolet B (280–320 nm,) radiation oir by cis–urocanic acid. Immunology 78: 99–104, 1993.

J.A. Ross, S.E. Howie, M. Norval, J. Maingay and T.J. Simpson. Ultraviolet–irradiated urocanic acid suppresses delayed type hypersensitivity to herpes simplex virus in mice. J. Invest. Dermatol. , 87: 630–633, 1986.

J.A. Ross, S.E. Howie, M. Norval and J.P. Maingay. Induction of suppression of delayed–type hypersensitivity to herpes simplex virus by epidermal cells exposed to UV–irradiated urocanic acid in vivo. Viral Immunol. 1(3): 191–197, 1987.

J. A. Ross et al., Two Phenotypically Distinct T Cells are Involved in Ultraviolet–Irradiated Urocanic Acid–Induced Suppression of the Efferent Delayed–Type Hypersensitivity Response to Herpes Simplex Virus, Type 1 In Vivo, J. Invest. Derma., vol. 89, No. 3, pp. 230–233 (1987).

FIG. 1

TRANSDERMAL TREATMENT WITH MAST CELL DEGRANULATING AGENTS FOR DRUG-INDUCED HYPERSENSITIVITY

This is a continuation of application Ser. No. 08/198,003, filed Feb. 17, 1994, which in turn is a continuation in part of U.S. Ser. No. 08/022,080, filed Feb. 25, 1993, both now abandoned.

1. FIELD OF THE INVENTION

The present invention in the field of drug delivery relates to methods and compositions for intervention in skin immune responses to prevent or inhibit undesired irritation or contact sensitization reactions caused by various therapeutic drugs delivered dermally or transdermally. This is achieved by local treatment of the area of the skin receiving the drug with a tolerizing or counter-sensitizing agent having mast cell degranulating activity, such as cis-urocanic acid, or an analogue or derivative thereof.

2. BACKGROUND OF THE INVENTION

2.1. Transdermal Drugs and Delivery Systems as Irritants and Sensitizers

The transdermal route of parenteral delivery of drugs provides many advantages over alternate routes of administration. Transdermal delivery systems (TDS) for delivery of drugs or other beneficial agents are well-known (see, for example, U.S. Pat. Nos. 3,598,122, 3,598,123, 4,286,592, 4,314,557, 4,379,454, 4,559,222 and 4,573,995, which are herein incorporated by reference). A TDS is generally composed of the following components: (a) "basic components," including backing, matrix reservoir, and an optional separate adhesive layer; (b) the drug; (c) "additives," including solubilizers, plasticizers and penetration enhancers; and (d) "impurities" such as residual amounts of monomers, initiators, cross-linkers, etc., from the polymerization process during fabrication of the basic components.

However, TDS provide conditions highly conducive for the induction of skin allergic reactions, and the following skin reactions may be expected to occur:

1. Irritant reactions to the drug, an additive, an impurity, or a combination thereof;
2. Allergic reactions, especially to the low molecular weight components (drug, additive, impurity, adhesive);
3. Prolonged skin occlusion causes blocking of sweat ducts favoring local sweat retention syndrome.

It is well known that many drugs, including some currently on the U.S. market, e.g., clonidine, sensitize the skin when used in a TDS. The skin inflammation produced by either the transdermally delivered drug, a non-irritating drug combined with skin irritating enhancers (discussed below), or a combination of an irritating or sensitizing drug and enhancer, may persist well beyond the time that the patch is removed from the skin. The local inflammation may be a source of discomfort and a clinical complication in a subject suffering from such a reaction.

Psoriasis-like changes have been noted in skin from subjects receiving propranolol and other beta blockers (Brigden, W. D. et al., *Brit. J. Dermatol.* 95:335 (1976); Gaylarde, P. M. et al., *Clin. Exp. Dermatol.* 3:157 (1978)). Workers handling alprenolol have shown signs of allergic dermatitis (Nater, J. P. et al., *Unwanted Effects of Cosmetics and Drugs Used in Dermatology*, Excerpta Medica, Amsterdam, 1985). A clonidine transdermal device (Catapress-TTS®) as well as clonidine in petrolatum, induced irritant reactions (Mailbach, H. I., *Contact Derm.* 12:192 (1985). Allergic contact dermatitis has been reported for nitroglycerine in a TDS (Transderm-Nitro) (Rosenfeld, A. S. et al., *Am. Heart J.* 108:1061 (1984); Fisher, A. A., *Cutis* 34:526 (1984)), where it was shown that the drug itself was the cause of the allergic response. Scopolamine delivery has been reported to induce delayed hypersensitivity reactions (Trozak, D. J., *J. Am. Acad. Dermatol.* 13:247–251 (1985); Van der Willigen, A. H. et al., *J. Am. Acad. Dermatol.* 18:146–147 (1988)). Bircher, A. J. et al., *Contact Derm.* 25:230–236 (1991) reported irritant reactions and contact sensitization to nicotine delivered in a TDS for the promotion of smoking cessation.

The main barrier to permeation of drugs through the skin is the stratum corneum. Depending on the drug, both keratin and lipids can contribute to the permeation or penetration barrier; these may be referred to as polar and nonpolar regions, respectively. Because hydration of the stratum corneum affects barrier function, water can be considered as an ideal nontoxic skin permeation enhancer. To augment the skin permeation of drugs, certain other agents, called skin permeation enhancers, are added to a TDS. Permeation enhancers have been defined as substances that increase the permeability of the skin without severe irritation or damage to its structure (Hadgraft, J., *Pharm. Into.* 5:252 (1984)). Permeation enhancers must penetrate at least into the stratum corneum to fulfill their role of reducing the barrier function of the skin for the transdermally administered drug. Thus, although ideal enhancers are non-toxic, non-allergic and nonirritating, in reality these compounds nevertheless induce skin irritation or contact sensitivity in some individuals, either alone or in conjunction with the therapeutic drug with which they are combined.

Excipients which are added to enhance the skin permeation of the transdermally delivered pharmacologically-active drugs may themselves act as skin irritants. For example, ethanol, used to enhance the delivery of estradiol is a well-known skin irritant (Ravnikar, V., *Am. J. Obstet. Gynecol.* 156:1332–1334 (1987)).

Nonionic surfactants, in particular polyoxyethylenes, used in TDS or considered useful as solubilizers, plasticizers or penetration promoters, caused irritation (Mezei, M. et al., *J. Pharm. Sci.* 59:129 (1970)). Methylmethacrylate, a starting material for polyacrylate-based TDS, showed dermatotoxic reactions upon dermal absorption (Kanerva, L. et al., *Arch. Toxicol. Suppl.* 9:456 (1986)).

In summary, it is a likely risk that many small molecules, once incorporated into a TDS, encounter ideal conditions for entering the viable epidermis and triggering an allergic response. This risk is enhanced due to a most basic property of almost all TDS: occlusivity.

2.2. Treatment of Drug-Induced Skin Sensitization

In reviewing the TDS field, Bodde, H. E. et al., *Crit. Rev. Ther. Drug Carrier Syst.* 6:87–115 (1989), listed a number of approaches for avoiding undesired drug side effects in the skin. Included in this list were the avoidance of irritating or sensitizing components, appropriate testing of allergenic drugs, avoidance of friction and pressure, and minimization of occlusion. The only pharmacotherapeutic approach, mentioned in passing, was the suppression of skin reactions by delivering antihistamines or cromolyn sodium by the TDS.

Others have addressed the problem of treating or preventing skin inflammation produced by the transdermal delivery of a skin-irritating and/or a skin-sensitizing drug. For example, Ross et al., U.S. Pat. No. 4,897,260 (30 Jan. 90), EP 0282156 and WO 88/09175 disclosed that the addition of glucocorticoid carboxylic acid esters, such as triamcinolone acetone 21-oic acid methyl ester, to percutaneous drug delivery devices suppressed the induction of cutaneous DH by a component in a percutaneous drug delivery system. Patel, D. C. et al., U.S. Pat. No. 4,855,294, disclosed that glycerin reduced mild skin irritation caused by drug permeation by drug permeation enhancers, such as alcohols, diols, oleic acid, and glycerol dioleate.

Cormier et al., U.S. Pat. No. 4,885,154 (5 Dec. 89) disclosed reduction in skin or mucosal sensitization or irritation by the transdermal coadministration, with a sensitizing or irritating drug, of a "metabolic modulator." Such modulators included tranylcypromine and phenyl alcohols, for example, as 2-phenyl-1 ethanol, 3-phenyl-1-propanol, 4-phenyl-1-butanol and cinnamyl alcohol. The basis of the choice of modulator was its ability to inhibit the enzyme that metabolizes the drug, which presumably prevented the generation of an irritating or allergenic drug metabolite. The combined administration of an immunogenic drug and such modulators also inhibited sensitization by the drug.

Amkraut et al., U.S. Pat. Nos. 5,000,956 (19 Mar. 91) and 5,077,054 (31 Dec. 91) disclose the use of a corticosteroid, co-extensively co-administered with a sensitizing agent, to prevent contact allergy induced by the transdermal delivery of a sensitizing drug. Preferred corticosteroids were hydrocortisone and its esters. Amkraut, U.S. Pat. Nos. 5,049,387 (17 Sep. 91) and 5,118,509 (2 Jun. 92), disclosed a method for inducing immune tolerance to a sensitizing drug by continuously and co-extensively co-administering to a skin or mucosal site the drug and a corticosteroid, preferably hydrocortisone or an ester thereof. After such a regimen, when the sensitizing drug is administered, the subject is non-reactive. Also disclosed are transdermal delivery systems for the tolerance producing combinations.

Ledger et al., U.S. Pat. No. 5,120,545 (9 Jun. 92) discloses a method for reducing or preventing skin sensitization by inhibiting the immunological processing of a transdermally sensitizing drug as an antigen. The method comprises co-administration to the skin or mucosa of the sensitizing drug and an agent which inhibits antigen processing. The inhibition of antigen processing could occur either in the induction phase or the elicitation phase of skin sensitization. Effective inhibiting agents were said to be those which raised the intracellular pH of low pH organelles, particularly the intralysosomal pH of antigen presenting cells in the skin. Examples of such agents are ionophores which interfere with ionic pumps and thereby allow intralysosomal pH to rise. Alternatively, inhibitors could be weak bases which accumulate and raise the pH in lysosomes. Example of such compounds are amphiphilic cations including amphiphilic amines such as ammonia and its salts (in particular ammonium chloride), low molecular weight amines and their salts, and amino alcohols, such as ethanolamine, diethanolamine, triethanolamine and tromethamine, and their salts.

Cormier et al., U.S. Pat. No. 5, 130,139 (14 Jul. 92), contains a disclosure similar to Ledger et al., supra, additionally disclosing the co-administration of a lysosomal uptake inhibiting agent to block sensitization with a weak base irritating drug. Preferred inhibiting agents were monensin and amphiphilic amines, including ammonium chloride. Ammonium chloride and monensin reduced the irritation induced by propranolol or chloroquine without inhibiting drug permeation into the skin.

South African Patent Application ZA 9006583 (to Beth Israel Hospital) discloses the use of the calcium channel blocker nifedipine as a countersensitizer and skin inflammation inhibitor. Nifedipine was shown to significantly reduce the inflammation caused by epicutaneously challenging mice previously sensitized with oxazolone.

Franz et al., U.S. Pat. No. 5,028,431 (2 Jul. 91) and EPO Publication No. 314528 (3 May 89), disclose methods and compositions for the administration of an anti-dermatitis agent in conjunction with a sensitizing or irritating drug in a controlled release or transdermal device to prevent irritation or sensitization. Examples of antidermatitis agents included corticosteroids, inhibitors and competitors of arachidonic acid metabolism, free radical scavengers, Vitamin E, nordihydroguiarietic acid, Vitamin D, and leukotriene receptor antagonists.

Govil, S. K. et al., U.S. Pat. No. 4,908,213 (Mar. 13, 1990) discloses the addition to a nicotine patch of an antipruritic agent selected from a group consisting of bisabolol, oils of chamomile, chamazulene, allantoin, D-panthenol, glycyrretenic acid, corticosteroids and antihistamines. These agents were said to counteract the pruritus which accompanied the delivery of nicotine.

German Patent Application DD297062 (to TKS Optinum) reports that magnesium salts have anti-inflammatory effects on allergic skin inflammation. Specifically, 28% magnesium chloride inhibited skin inflammation in mice induced by contact with 0.5% dinitrochlorobenzene.

Alternative and improved compositions and methods which could facilitate transdermal delivery of drugs with decreased sensitization and inflammation would be useful additions to the art.

2.3. The Immune System and Delayed Hypersensitivity Responses

One type of immune response commonly generated against an antigen which enters via the skin is known generically as the delayed-type hypersensitivity (DH) reaction. DH reactions, as well as other types of immune responses, involve the action of "antigen presenting cells" (APCS) which internalize and process antigen and present the processed antigen on the cell surface in an "immunogenic" form in physical association with glycoproteins of the major histocompatibility complex (MHC) known as class II molecules. This MHC-associated antigen is recognized by, and stimulatory toward, antigen-specific T lymphocytes.

T lymphocytes, recognize and bind to the processed antigen by means of their T cell antigen receptor (TCR) and respond by differentiating and proliferating, which results in the generation of antigen-specific effector cells. Also generated during the course of such a response are antigen-specific memory T cells which are retained in the body and stand poised to respond to a future encounter with the same antigen. A later encounter with the same antigen activates such memory T cells, resulting in a more rapid and more vigorous immune response.

An animal can be rendered specifically unresponsive to an antigen, a state known as immunological tolerance, in many different ways (see, for example Roitt, I., *Essential Immunology*, 6th Ed., Slackwell Scientific Publications, Oxford (1988); Klein, J., *Immunology*, Blackwell Scientific Publications, Inc., Cambridge, Mass., (1990). A number of mechanisms are thought to be responsible for the induction and maintenance of this tolerant state. Regardless of mechanism, it is well-known that tolerance to an antigen which stimulates a DH response can be induced by first presenting the antigen in a tolerogenic form or via a tolerogenic route. For example, presentation of antigen following, or in conjunction with, a drug which suppresses the immune response may result in a state of prolonged or even permanent immunological tolerance.

2.4. Immunology of the Skin

For a general discussion, see, for example, Klein, J., *Immunology*, Blackwell Scientific Publications, Inc., Cambridge, Mass., 1990, pp. 451–459; Streilein, J. W., *J. Invest. Dermatol.* 80:12s–16s (1983). The major APCs in the skin are the Langerhans cells (Streilein, J. W., supra) and dermal dendritic cells. An antigen delivered to the skin from the outside (epicutaneously) or into the skin (intracutaneously or intradermally), whether it be from an encounter with a poison ivy plant or a transdermally applied drug, reaches the Langerhans cells and other APCs which process and present the antigen to T lymphocytes. The T cells produce a T cell-mediated immune response of the DH type. Thus, if a transdermally delivered drug has sensitized the immune system, a future attempt at transdermal delivery of the same drug will evoke a potent, local and destructive DH response in the skin. Such cutaneous DH responses, which have a strong inflammatory component, have been known by various names, including contact sensitization, contact hypersensitivity or allergic contact dermatitis. Such a state of drug-specific immunity precludes further transdermal delivery of the same drug.

Irradiation of skin with ultraviolet light B (UVB) is known to be immunosuppressive (Greene, M. I. et al., *Proc. Natl. Acad. Sci. USA* 76:6592 (1979); Noonan, F. P. et al., *Photochem. Photobiol.* 34:683 (1981); Noonan, F. P. et al., *Immunology* 43:527 (1981); Noonan, F. P. et al., *J. Immunol.* 132:2408 (1984); Kripke, M. L. et al. *J. Immunol.* 137:443 (1986); Yoskikawa, T. et al., *J. Invest. Dermatol.* 95:530 (1990)). These UVB effects are thought to be mediated, in part, the UVB-induced isomerization of trans-urocanic acid (trans-UCA), a molecule which makes up about 0.5% of the total dry weight in the upper layers of human epidermis, to cis-urocanic acid (cis-UCA) (Noonan, F. P. et al., *J. Invest. Dermatol.* 84:342 abstr. (1985). cis-UCA is known to have various immunosuppressive actions in vivo in a number of experimental systems (Noonan, F. P. et al., *J. Invest. Dermatol.* 90:92 (1988); Ross, J. A. et al., *J. Invest. Dermatol.* 87:630 (1986); Ross, J. A. et al., *J. Invest. Dermatol.* 89:230 (1987); Ross, J. A. et al., *Viral Immunol.* 1:191 1987/88); Reeve, V. E. et al., *Photochem. Photobiol.* 49:459–464 (1989). cis-UCA may act through histamine-like receptors in the skin (Norval, M. et al., *Photodermatol. Photoimmunol. Photomed.* 7:243–248 (1990)). More recently, Kurimoto, I. et al., *J. Immunol.* 148:3072–3078 (1992) showed that the UVB impairment of the induction of contact sensitivity to epicutaneously applied haptens in certain mouse strains depended on the participation of the cytokine, tumor necrosis factora (TNFa). The authors suggested that local release of TNFa may inhibit sensitization by trapping epidermal Langerhans cells and preventing them from reaching the draining lymph node where they activate T cells.

Despite the foregoing, it remains unknown whether mast cell degranulators, e.g., cis-UCA, can act in the pharmaceutical setting by inhibiting sensitization by drugs applied dermally or transdermally and therefore, whether these materials have utility as immunologically tolerizing and counter-sensitizing agents in man.

3. SUMMARY OF THE INVENTION

Compositions, articles and methods useful for preventing or inhibiting the effects of a skin irritating or skin sensitizing component of a transdermal drug delivery system are disclosed. Agents capable of inducing mast cell degranulation have been found by the present inventors to be useful in inducing immune tolerance, as countersensitizing agents, as well as anti-inflammatory agents.

Thus, present methods include administration before, during or after transdermal drug delivery of a mast cell degranulating agent to effect countersensitization. Alternatively, such agents can be administered prior to, at the onset of, or both prior to and along with, transdermal drug delivery produce a state of immunological tolerance which is sustained and protects the tolerant subject from sensitization upon subsequent exposure to the sensitizing drug or substance. The countersensitizing agent of the present invention is preferably capable of permeating the epidermis and is preferably administered transdermally. Novel methods and compositions containing cis-UCA, its analogues or metabolites, and providing anti-inflammatory effect are also disclosed.

Thus the present invention is directed to a method for preventing or inhibiting the skin irritating or skin sensitizing effect of a drug administered to the skin, which method comprises administering before, together with, before and together with, or after the drug, an effective amount of at least one mast cell degranulating agent.

Also provided is a method for preventing or inhibiting the skin irritating or skin sensitizing effect of a component of a transdermal drug delivery system, which method comprises administering before, together with, before and together with, or after the component, an effective amount of at least one mast cell degranulating agent. The skin irritating or sensitizing component may be a transdermally delivered therapeutic drug, a skin permeation enhancing substance, or a combination of the two.

In the above method, the at least one mast cell degranulating agent is preferably administered transdermally, together with the component.

The mast cell mast cell degranulating agent useful in the above methods is preferably selected from the group consisting of: (a) cis-urocanic acid, or an analogue or a metabolite thereof; (b) chloroquine; (c) capsaicin; (d) morphine sulfate; (e) a sodium channel ionophore; (f) a calcium channel ionophore; (g) an inhibitor of $Na^+/K^+$ channel ATPase; (h) quinine; (i) 4-aminopyridine; (j) an anti-human IgE antibody; (k) compound 48/80; (l) substance P; (m) estradiol; (n) somatostatin; (o) clonidine; (p) progesterone; (q) carbachol; and (r) spantide Preferred cis-urocanic acid analogue for use in the above methods include, but are not limited to: (a) a cis or trans isomer of 1-furanacrylic acid; (b) a cis or trans isomer of 2-pyrrole acrylic acid; (c) a cis or trans isomer of 2-thiopheneacrylic acid; and (d) dihydrourocanic acid.

Preferred cis-urocanic acid metabolite for use in the above methods include, but are not limited to: (a) histamine; (b) $N^1$-methylhistamine; (c) $N^1$-methylhistidine; (d) histidine; (e) imidazolepyruvic acid; (f) $N^3$-methylhistidine; (g) imidazoleacetic acid; (h) hydantoin 5-propionic acid; and (i) imidazolonepropionic acid.

The above methods are useful for treating or preventing skin irritation or skin sensitization produced by a drug selected from, but not limited to, the following group: (a) an angiotensin converting enzyme inhibitor; (b) a beta adrenergic receptor blocker; (c) an anti-hypertensive drug other than an angiotensin converting enzyme inhibitor or a beta adrenergic receptor blocker; (d) an anti-histamine; (e) an anti-asthmatic; (f) a non-steroidal anti-inflammatory drug; (g) a central nervous system active drug; (h) a weight control drug; (i) an anticoagulant; (j) a potassium control drug; (k) an immunomodulatory drug; and (l) a decongestant.

The above methods are useful for treating or preventing skin irritation or skin sensitization produced by a skin permeation enhancing substance selected from, but not limited to, the following group: ethanol, oleic acid, oleyl alcohol, linoleic acid, propylene glycol, lauramidopropyl betaine, dimethylsulfoxide, dimethylformamide, decylmethylsulfoxide, N-methylpyrrolidone, isopropyl alcohol, t-butanol and sodium lauryl sulfate.

The present invention further provides an article useful for preventing or inhibiting the skin irritating or skin sensitizing effect of a component of a transdermal drug delivery system, where the component is either a drug, a skin permeation enhancer or a combination of the two, the article comprising:

(a) a transdermal delivery system comprising a therapeutic drug of interest; and (b) an effective amount of at least one mast cell degranulating agent, preferably included in the transdermal delivery system (a).

In the above article, the mast cell degranulating agent is preferably selected from the group consisting of: (a) cis-urocanic acid, or an analogue or a metabolite thereof; (b) chloroquine; (c) capsaicin; (d) morphine sulfate; (e) a sodium channel ionophore; (f) a calcium channel ionophore; (g) an inhibitor of $Na^+/K^+$ channel ATPase; (h) quinine; (i) 4-aminopyridine; (j) an anti-human IgE antibody; (k) compound 48/80; (l) substance P; (m) estradiol; (n) somatostatin; (o) clonidine; (p) progesterone; (q) carbachol; and (r) spantide.

The sensitizing or irritating drug for which the above article is useful includes, but is not limited to, a member of the following group: (a) an angiotensin converting enzyme inhibitor; (b) a beta adrenergic receptor blocker; (c) an antihypertensive drug other than an angiotensin converting enzyme inhibitor or a beta adrenergic receptor blocker; (d) an anti-histamine; (e) an anti-asthmatic; (f) a non-steroidal anti-inflammatory drug; (g) a central nervous system active drug; (h) a weight control drug; (i) an anticoagulant; (j) a potassium control drug; (k) an immunomodulatory drug; and (l) a decongestant.

The irritating or sensitizing skin permeation enhancing substances for which the above article is useful include, but are not limited to, ethanol, oleic acid, oleyl alcohol, linoleic acid, propylene glycol, lauramidopropyl betaine, dimethylsulfoxide, dimethylformamide, decylmethylsulfoxide, N-methylpyrrolidone, isopropyl alcohol, t-butanol, and sodium lauryl sulfate.

In another embodiment, the present invention is directed to a pharmaceutical composition useful for preventing or inhibiting the skin irritating or skin sensitizing effect of a component of a transdermal drug delivery system, or inducing tolerance to the component, the composition comprising:

an effective amount of at least one mast cell degranulating agent and an acceptable pharmaceutical carrier.

In the above pharmaceutical composition, the mast cell degranulating agent is preferably selected from the group consisting of: (a) cis-urocanic acid, or an analogue or a metabolite thereof; (b) chloroquine; (c) capsaicin; (d) morphine sulfate; (e) a sodium channel ionophore; (f) a calcium channel ionophore; (g) an inhibitor of $Na^+/K^+$ channel ATPase; (h) quinine; (i) 4-aminopyridine; (j) an anti-human IgE antibody; (k) compound 48/80; (l) substance P; (m) estradiol; (n) somatostatin; (o) clonidine; (p) progesterone; (q) carbachol; and (r) spantide. The mast cell degranulating agent is most preferably cis-urocanic acid, or an analogue or a metabolite thereof.

A preferred cis-urocanic acid analogue for the above pharmaceutical composition includes, but is not limited to: (a) a cis or trans isomer of 1-furanacrylic acid; (b) a cis or trans isomer of 2-pyrrole acrylic acid; (c) a cis or trans isomer of 2-thiopheneacrylic acid; and (d) dihydrourocanic acid.

A preferred cis-urocanic acid metabolite for the above pharmaceutical composition, includes, but is not limited to: (a) histamine; (b) $N^1$methylhistamine; (c) $N^1$-methylhistidine; (d) histidine; (e) imidazolepyruvic acid; (f) $N^3$methylhistidine; (g) imidazoleacetic acid; (h) hydantoin 5-propionic acid; and (i) imidazolonepropionic acid.

Preferably, in the above pharmaceutical composition, the mast cell degranulating agent is in a form for transdermal administration, more preferably, by inclusion in a transdermal delivery system.

The present invention also provides a method for inhibiting an inflammatory reaction in the skin of a subject associated with an allergic or skin sensitizing reaction, which method comprises administering to the subject an effective amount of at least one mast cell degranulating agent. The at least one mast cell degranulating agent is preferably selected from the group consisting of cis-urocanic acid or an analogue or a metabolite thereof; chloroquine; capsaicin; morphine sulfate; a sodium channel ionophore; a calcium channel ionophore; an inhibitor of Na+/K+channel ATPase; quinine; 4-aminopyridine; an anti-human IgE antibody; compound 48/80; substance P; estradiol; somatostatin; clonidine; progesterone; carbachol; and spantide.

Also provided is a method for inducing immunological tolerance in a subject to a skin sensitizing drug or agent administered to the skin, which method comprises administering to the subject prior to, at the onset of, or both prior to and at the onset of, transdermal delivery of the sensitizing drug or agent, an effective amount of at least one mast cell degranulating agent. The at least one mast cell degranulating agent is preferably selected from the group consisting of cis-urocanic acid or an analogue or a metabolite thereof; chloroquine; capsaicin; morphine sulfate; a sodium channel ionophore; a calcium channel ionophore; an inhibitor of $Na^+/K^+$ channel ATPase; quinine; 4-aminopyridine; an anti-human IgE antibody; compound 48/80; substance P; estradiol; somatostatin; clonidine; progesterone; carbachol; and spantide.

In the above methods, the skin sensitizing drug or agent may be a transdermally delivered therapeutic drug, a skin permeation enhancing substance, an excipient or a combination thereof.

5. DETAILED DESCRIPTION OF THE INVENTION

The present inventors have discovered that agents capable of inducing a state of immunological tolerance, which renders the immune system specifically unreactive, or hyporeactive, to a particular sensitizing agent for a prolonged period. This class of agents is also capable of inducing mast cell degranulation are useful as countersensitizers when administered before, together with, or after, a transdermally delivered sensitizing drug. Thus one or a few presentations of the agent of the present invention, prior to, along with, or both prior to and along with, the sensitizing agent can render the subject immunologically tolerant to the sensitizing agent.

The present invention is thus directed to a method for preventing or inhibiting the skin irritating or skin sensitizing effect of a component of a dermal or transdermal drug delivery system, the method comprising administering before, together with, or after the component, an effective amount of at least one countersensitizing agent which agent can induce mast cell degranulation.

The skin sensitizing or irritating component of a TDS can be a transdermally delivered therapeutic drug, one or more skin permeation enhancers present in the TDS to enhance uptake of the therapeutic drug, or by a combination of the skin penetration enhancer or enhancers with the therapeutic drug or drugs in the transdermal composition.

Preferably, in the above countersensitization method the countersensitizing, mast cell degranulating agent is administered prior to, or together with, the component.

In the above tolerization method, the agent can be administered prior to, at the onset of, or both prior to and at the onset of, transdermal drug delivery to provide a sustained state of immune tolerance. Such a state of tolerance is characterized by the fact that the initial treatment or treatments with the agent of the present invention, which may be co-delivered with the drug, is sufficient to prevent skin sensitizing effects of any of a number of subsequent transdermal drug deliveries without further need to administer the agent.

Any agent capable of inducing mast cell degranulation can be employed according to the present invention. Suitable agents include, but are not limited to, cis-urocanic acid or analogues or metabolites thereof, chloroquine, capsaicin, morphine sulfate, sodium and calcium channel ionophores, inhibitors of $Na^+/K^+$ channel ATPase (such as tridecylresorcylic acid), quinine, 4-aminopyridine, an anti-human IgE antibody, compound 48/80, substance P, spantide and the like.

Preferably, the countersensitizing and mast cell degranulating agent is able to permeate the epidermis, for example, following administration via transdermal delivery. Accordingly, the preferred agents of the present invention have a molecular weight of 600 daltons or less and have a melting point of about 300° C. or less. Most preferably the agent is cis-urocanic acid or an analog or metabolite thereof. Unexpectedly, cis-urocanic acid has also been found to provide an anti-inflammatory effect.

5.1. Locally Acting Immunosuppressive Agents: Counter Irritants and Counter Sensitizers The terms "counter-sensitizer" or "counter-sensitizing agent", as used herein define a class of locally-acting immunosuppressive agents which are characterized by activity of causing degranulation of cutaneous mast cells. Degranulation of mast cells by the agents of the present invention results in localized selective release of TNFa as well as other compounds. This localized release of TNFa serves to counteract sensitization by an antigen, such as the transdermally delivered drug.

Such agents thus act early in the immune response, and thereby inhibit or prevent the development of skin irritation and/or skin sensitization by a transdermally delivered drug. The counter-sensitizing agents are useful alone or in combination as additives to transdermal drug delivery composition. The inclusion of a counter-sensitizing agent of the present invention eliminates or minimizes skin irritation and sensitization induced by an irritant or immunogenic drug delivered transdermally.

As mentioned above, one group of useful countersensitizing agents of the present invention includes cis-UCA, its analogues and metabolites. Preferred cis-UCA analogues include, but are not limited to, cis and trans isomers of 2-methylurocanic acid, cis- and trans- isomers of 2-furanacrylic acid, cis- and trans-isomers of 2-pyrroleacrylic acid, cis- and trans-isomers of 2-thiopheneacrylic acid and 3-thiopheneacrylic acid, and cis- and trans- isomers of dihydrourocanic acid.

Figure 1:
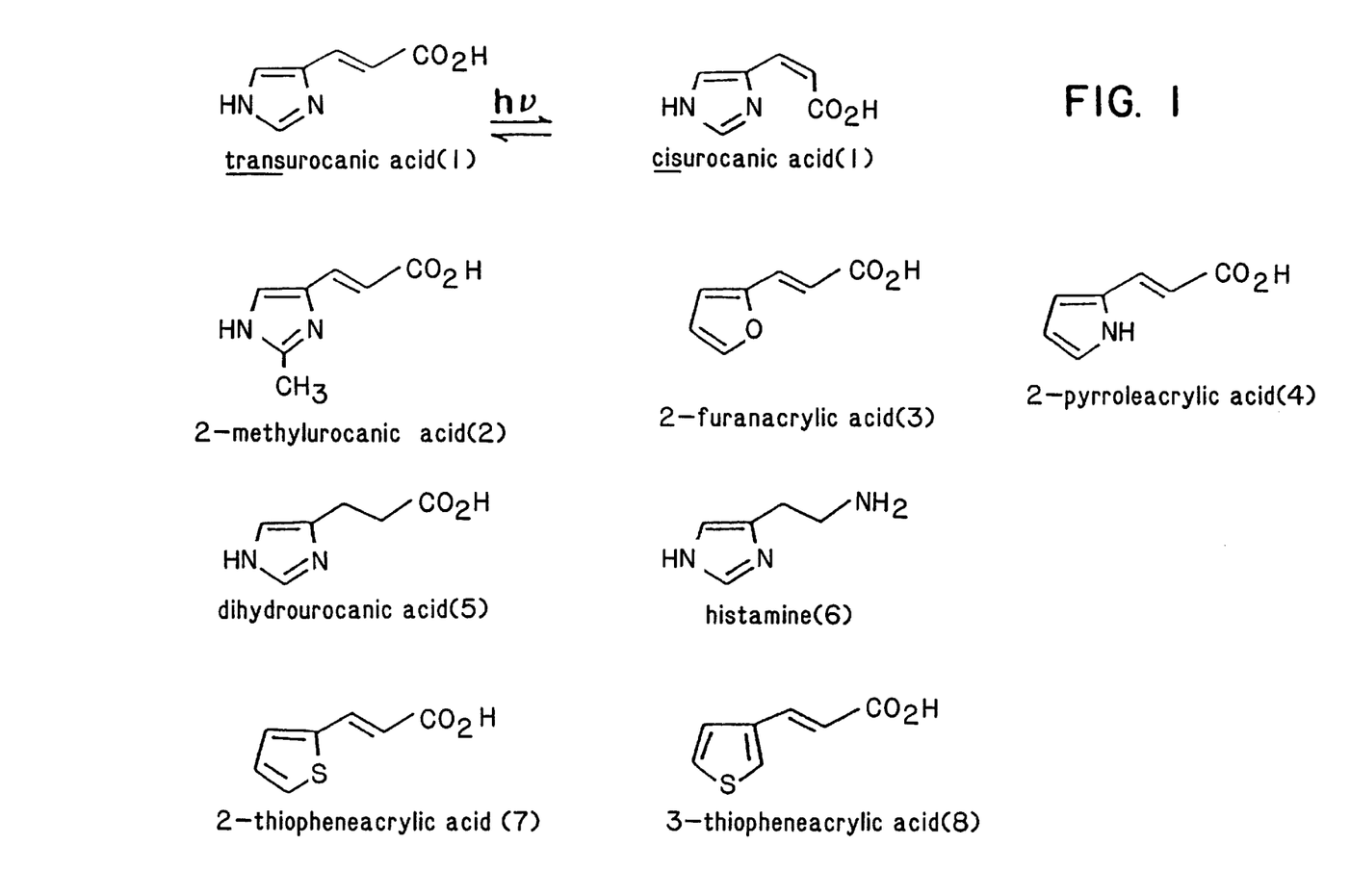
FIG. 1 provides the structural formulae for both the cis-UCA (also called the "Z-form" or Z-urocanic acid) and trans-UCA (also called the "E-form" or E-urocanic acid). Also shown are the chemical structures of cis- and trans-UCA as well as a number of analogues of cis-UCA.

Referring to FIG. 1, the trans isomer of 2-methylurocanic acid (Compound 2) is prepared according to Gerlinger, E. et al., *Tetrachemistry* 21:3523–3528 (1983), and is converted to the cis isomer by UV irradiation as described herein for UCA. The trans-isomer of 2-furanacrylic acid (Compound 3) may be prepared by the reaction of furfuraldehyde with acetic anhydride in the presence of potassium acetate (Ailen, C. F. H., *Organic Synthesis*, vol. 20, pp. 55–56, J. Wiley, New York, 1940) and may be converted to the cis isomer as described herein for UCA. The cis isomer of 2-pyrroleacrylic acid (Compound 4) may be prepared by hydrolysis of pyrrolizin-3-one (McNab, H., *J. Org. Chem.* 46:2809 (1981)) using 2N sodium hydroxide in tetrahydrofuran. The trans isomer may be prepared by Knoevenagel condensation of 2-pyrrolecarboxaldehyde with malonic acid in the presence of piperidine. Dihydrourocanic acid (Compound 5) may be prepared by catalytic hydrogenation of trans-UCA in methanol in the presence of palladium charcoal catalyst. After filtration of the catalyst and removal of solvent, the pure dihydrourocanic acid is obtained. The trans isomers of 2-thiopheneacrylic acid and 3-thiopheneacrylic acid (Compounds 7 and 8) may be prepared from the corresponding aldehydes by Knoevenagel condensation as for trans-2-pyrroleacrylic acid, above, and isomerized to give the cis-isomers.

Preferred cis-UCA metabolites include, but are not limited to, histamine, $N^1$-methylhistamine, $N^1$-methylhistidine, histidine, imidazolepyruvic acid, $N^3$-methylhistidine, imidazoleacetic acid, hydantoin 5-propionic acid and imidazolonepropionic acid.

5.2. Drugs Which Sensitize Transdermally

A large number of drugs are capable of producing cutaneous hypersensitivity when they are delivered via the transdermal route. Thus, this particularly advantageous form of drug administration must be stopped in those individuals in whom such immunity has been triggered. The methods and compositions of the present invention are useful for prevention or inhibition of sensitization produced by transdermal delivery of known sensitizing drugs such as clonidine, tetracaine, naloxone, naltrexone, nalbutaphine, narcotic analgesics such as puprenorphine, hydroporphone and levorphanol.

This invention is also useful in connection with the delivery of drugs within the broad class normally delivered through the body surfaces and membranes, in particular through the skin. This includes therapeutic agents in all of the major therapeutic areas, including, but not limited to: anti-infectives, such as antibiotics and antivirals; analgesics and analgesic combinations; anorexics; antiarthritics; anti-asthmatics (such as albuterol, metaproterenol, ketotifen and terbutaline); anticoagulants (such as urokinase); anticonvulsants; antidepressants; anti-diabetics; antidiarrheals; antihistamines (such as chlorpheniramine and diphenhydramine); anti-inflammatory agents (such as ketoprofen, prostaglandins, flurbiprofen, diclofenac, indomethacin, piroxicam and ibuprofen); antimigraine agents; anti-motion sickness preparations; antinauseants; antineoplastics; antiparkinsonism drugs; antipruritics, antipsychotics; antipyretics; antispasmodics, including gastrointestinal and urinary;

anticholinergics; sympathomimetics; xanthine derivatives; cardiovascular agents, including angiotensin converting enzyme inhibitors (such as captropril and fosinopril), calcium channel blockers, beta blockers (such as nadolol, timolol, propranolol and alprenolol), antiarrythmics, antihypertensives (such as clonidine), diuretics, vasodilators, including general, coronary, peripheral and cerebral; central nervous acting agents (such as fluphenazine, trifluperazine, haloperidol, Xanax®, Librium®, Valium®); cough and cold preparations; decongestants; diagnostics; hormones; hypnotics; muscle relaxants; parasympatholytics; parasympathomimetics; psychostimulants; sedatives; weight control and appetite suppressive drugs (such as mazindol) and tranquilizers.

5.3. Skin Permeation Enhancers Which Irritate or Sensitize Transdermally

Skin permeation enhancers, substances that increase the permeability of the skin without severe irritation or damage to its structure (Hadgraft, J., supra), are commonly added to a TDS. Permeation enhancers may also induce skin irritation or contact sensitivity in some individuals, either alone or in conjunction with the therapeutic drug with which they are combined.

The present invention is also intended to be used to counteract such unwanted effects of the skin permeation enhancing agents. Non-limiting examples of skin irritating chemical enhancers include ethanol, oleic acid, oleyl alcohol, linoleic acid, propylene glycol, lauramidopropyl betaine, 2-pyrollidone, N-methyl pyrrolidone, N-methyl formamide, dimethylsulfoxide, dimethylformamide, decylmethylsulfoxide, isopropyl alcohol, t-butanol, and sodium lauryl sulfate.

These permeation enhancers can be divided into three basic categories (Barry, B. W., *Int'l. Conf. Controlled Release Bioact. Mater.* 13:136 (1986); Barry, B. W., *J. Controlled Release* 6:85 (1987)):

1. Enhancers which promote permeation through both polar and lipid regions, e.g., 2-pyrollidone, N-methyl pyrrolidone and N-methyl formamide;
2. Accelerants which preferentially affect the polar pathway, e.g., propylene glycol plus decylmethyl sulfoxide; and
3. Permeation enhancers which mainly modify the lipid route, e.g., propylene glycol and propylene glycol+ oleic acid.

Combinations of permeation enhancers are sometimes necessary to obtain the desired effect.

5.4. Application of Counter-Sensitizing Agents

One or more of the counter-sensitizing agents of the present invention, as described above, is administered with a therapeutic drug or drug combination. The counter-sensitizing agent may be administered topically. In a preferred embodiment, the counter-sensitizing agent is administered in a transdermal or a controlled-release device. Examples of transdermal devices and delivery systems are disclosed in Bodde, H. E. et al., *Crit. Rev. Ther. Drug Carrier Syst.* 6:87–115 (1989); and in U.S. Pat. Nos. 3,598,122, 3,598,123, 4,286,592, 4,314,557, 4,379,454, 4,559,222, 4,573,995, which references are hereby incorporated by reference.

The precise formulation of the transdermally administered drug and the counter-sensitizing agent of the present invention can be designed to deliver the drug and the counter-sensitizing agent at the desired fluxes and can be in numerous forms, including, without limitation, ointments gels and creams. Aqueous formulations, in particular gels, typically comprise water and about 1–2% (w/w) of a gelling agent such as hydroxyethyl cellulose or hydroxypropyl cellulose. Typical non-aqueous gels comprise silicone fluid or mineral oil. The mineral oil may also have 1–2% (w/w) of a gelling agent such as colloidal silicon dioxide. The suitability of a particular gel composition depends on the compatibility of its constituents with the sensitizing drug (with or without a permeation enhancer) and the counter-sensitizing agent.

In another embodiment, one or more counter-sensitizing agents of the present invention is delivered to the skin prior to the administration of the therapeutic drug or drugs. Such prior administration can be via transdermal application using a device as described above, via direct topical application, intracutaneous injection, and the like.

In yet another embodiment, one or more counter-sensitizing agents is delivered by another non-cutaneous route and method of delivery, either concurrently with, or prior to, the transdermal administration of the therapeutic drug. Examples of such administration include subcutaneous, intravenous, intramuscular, or intraperitoneal routes. Alternatively, or concurrently, administration may be by the oral route.

In all of the above embodiments, the dosage of counter-sensitizing agent administered will be dependent upon the agent, the age, health, and weight of the recipient, kind of concurrent treatment, if any, frequency of treatment.

The methods and compositions within the scope of this invention include all compositions and methods wherein the counter-sensitizing agent is contained in an amount effective to achieve its intended purpose. While individual needs vary, determination of optimal ranges of effective amounts of each component is within the skill of the art.

For transdermal administration, typical effective dosages of the counter-sensitizing agent to prevent sensitization by a sensitizing drug will depend on it permeation through human skin, and is a function of the physical properties of the permeant, including the partition coefficient of the permeant between solvent and skin, molecular weight and melting point. In general, the maximal flux that can be obtained from any permeant occurs from saturated solutions. Equations have been derived that predict accurately the maximal flux given the partition coefficient, molecular weight and melting point of the permeant as described elsewhere ("TREATISE ON CONTROLLED DRUG DELIVERY," A. Kydonieus, ed., Marcel Dekker, Inc., New York, 1991, in particular, p. 370, equations 3a and 4a, and p. 34, FIG. 2). For example, for the transdermal delivery of a most preferred counter-sensitizing agent, cis-UCA, the expected maximal flux that can be delivered locally to skin is in the range of 1–50 $\mu g/cm^2/hr$. This value is dependent, for example on varying skin age, skin type and skin condition. Preferably the range is 5–25 $\mu g/cm^2/hr$. Accordingly, as will be understood by those skilled in the art, the delivery of a particular counter-sensitizing agent, for example, cis-UCA, is controlled by the percent saturation of that agent in the chosen vehicle.

6. PREPARATION OF cis-UROCANIC ACID

Preparations containing cis-UCA are known and can be made using known methodology. For example, solutions containing trans-UCA can be subjected to photoisomerization to substantially convert the trans form to the cis-form. Any suitable solvents, aqueous, nonaqueous or mixtures thereof, can be used to prepare any desired concentrations which are optionally buffered to pH between 1 and 12. Typically, solutions containing between about 1 to about 5 mg/ml of trans-UCA (commercially available from, for example, Sigma Chem. Co.) in a solvent, e.g., water, are used.

EXAMPLE 1

Preparation of cis-UCA-Containing Solution

A. Trans-UCA Solutions

Three liters of deionized, distilled water were heated to 40° C. trans-UCA (9 g; Sigma) was added slowly to the heated water and thereafter the solution was stirred at room temperature for 3 hours. The solution was filtered, transferred to sealed containers under sterilized conditions and allowed to equilibrate at room temperature for 6 hours.

B. Photoisomerization to cis-Urocanic Acid

The above trans-UCA solution was irradiated with a UV-cross linker box (Spectronic Corp.) equipped with six UV tubes emitting light maximally at a wavelength of 313 nanometers. The irradiation intensity was 90 watts/hour for 3 hour intervals. Between intervals, samples were taken and tested chromatographically to determine the amount of conversion to the cis-form. After a total of 2000 joules/cm$^2$, the irradiation was stopped yielding a solution containing a cis/trans ratio of 70:30. This sample was used for the tests described below.

EXAMPLE 2

Percutaneous Permeation of Urocanic Acid Through Human Skin

A. Experimental Procedures

Skin permeation experiments were undertaken to measure the flux of cis-UCA and the trans-UCA) through human skin. This information is required for topical delivery of cis-UCA using a TDS.

cis-UCA was prepared by ultraviolet irradiation of solutions of trans-UCA (obtained from Sigma Chemical Co., St. Louis, Mo.), as described above (see Example 1 above).

For skin permeation experiments, human cadaver skin was obtained and sectioned on a dermatome to yield a partial thickness skin of about 400 $\mu$m. Partial thickness skin samples were transferred to standard Franz cell diffusion chambers with the stratum corneum side up, and equilibrated with phosphate buffered saline (PBS) at pH 7.2. at 35° C. in standard thermal blocks (Pierce Reacti-Therm).

B. Recovery of Urocanic Acid Isomers After Skin Permeation

Three different solution of UV-irradiated UCA were prepared. All samples were mixtures of both cis-UCA and trans-UCA, contained about between 55% to 67% cis-UCA. The three different solutions (0.5 ml) were applied to the skin samples in the donor chamber of the diffusion chamber, and fractions of the receptor solution (saline) were collected and the amount of cis and trans isomers that permeated through the skin determined by standard HPLC methods. One hundred and eight hours post-incubation at 35° C., the remaining UCA in the donor chamber was collected and the tissue homogenized and extracted with base (0.5N KOH). The tissue extracts were neutralized and aliquots analyzed by HPLC.

The recovery of the cis- and trans- isomers in the receptor and donor chambers, the amount retained in the tissue, and the total recovery are all shown in Table I, below. The recovery of UCA isomers in this system was quantitative and amounted to over 90% of the applied dose.

Most of the applied UCA acid did not permeate and was recovered in the donor chamber of the diffusion cells. The fraction that permeated accounted for only 1.05% of sample-I, 1.48% of sample-II, and 15.14% of sample-III.

trans-UCA and cis-UCA permeated human skin at rates which were functions of dosage form and concentration in the applied dosages. Sample I showed the slowest overall permeation rate of 0.169 $\mu$g/cm$^2$/hr for both trans- and cis-UCA. The combined permeation rate of trans and cis UCA from, sample II was 1.08 $\mu$g/cm$^2$/hr and that for sample III was 26.74 $\mu$g/cm$^2$/hr.

TABLE I

SUMMARY OF THE RECOVERY OF UROCANIC ACID ISOMERS IN THE SKIN PERMEATION STUDY

| SAMPLE ID | AMOUNT TESTED (mg/ml) | Z-UCA (%) | Receptor ($\mu$g) | Donor ($\mu$g) | Tissues ($\mu$g) | Total Recovery % |
|---|---|---|---|---|---|---|
| I | 5.147 | 67 | 25 | 2,318 | 47 | 92.85 |
| II | 15.624 | 55 | 106 | 7,001 | 55 | 91.67 |
| III | 36.148 | 67 | 2713 | 13,897 | 203 | 93.02 |

Table II, below shows the fluxes of UCA isomers through human skin. Both trans-UCA and cis-UCA permeated human skin at comparable fluxes. The overall flux for sample I was 0.17 $\mu$g/cm$^2$/hr, for sample II 1.08 $\mu$g/cm$^2$/hr, and 25.7 $\mu$g/cm$^2$/hr for sample III.

The observed fluxes for the cis- and trans-isomers of UCA were in the range of calculated values (5–10 $\mu$g/cm$^2$/hr) for flux rates derived from equations developed to predict flux through human skin. For further details see Kydonieus, A. (ed.), supra.

TABLE II

SUMMARY OF FLUXES OF UROCANIC ACID ISOMERS THROUGH HUMAN PARTIAL THICKNESS SKIN

| SAMPLE ID | Z-ISOMER ($\mu$g/cm$^2$/hr) | E-ISOMER ($\mu$g/cm$^2$/hr) | RATIO (Z/E) | OVERALL FLUX ($\mu$g/cm$^2$/hr) |
|---|---|---|---|---|
| I | 0.0987 | 0.0676 | 1.46 | 0.1690 |
| II | 0.5825 | 0.4765 | 1.22 | 1.0839 |
| III | 19.5648 | 7.2327 | 2.71 | 26.7138 |

EXAMPLE 3

Biological Activity of Cis-UCA: Inhibition of Contact Hypersensitivity

The mast cell degranulating agent, cis-UCA was tested for its ability to act as a countersensitizer.

Test Animals

BALB/c female mice were maintained in a specific pathogen-free colony. Age-matched mice between 8 and 12 weeks of age were maintained in filter-protected cages and fed mouse chow and water ad libitum. Lighting was controlled to provide 12 hours light-dark cycles.

Experimental Procedures

A. Induction of Sensitization

A 7% (w/v) working solution of trinitrobenzene sulfonate (TNBS) was prepared in distilled water. Previous studies showed that this water-soluble hapten efficiently sensitizes Balb/c mice (Streilein, 1992). For induction of sensitization, each of 5 Balb/c mice received epicutaneous application of 35 $\mu$g of TNBS via a Hilltop chamber for 5 hours.

B. Elicitation of Responses

A contact hypersensitivity response was elicited on day 5 by challenging the right ear of each mouse with 20 $\mu$l of 1% trinitronchlorobenzene (TNCB) (in acetone). Ear thickness was measured with a spring-loaded caliper immediately before challenge, and at 24 and 48 hours after challenge. Ear thickness was measured in mm×$10^{-3}$.

The statistical significance of differences in the contact hypersensitivity response between control and treated mice was determined using Student's t test for two independent variables. Each group contained five mice. Negative control mice were treated for 24 hours with 100 μl of PBS, pH 5.5, and challenged on the right ear 5 days later with 20 μl of 1% TNCB.

RESULTS

C. Pretreatment vs. Pretreatment Plus Co-administration of ciS-UCA

For pretreatment, 100 μl of a 6% solution of UV-irradiated UCA (70% cis and 30% trans as determined by HPLC analysis) in PBS, pH 5.5, was placed in a Hilltop chamber, and applied on the shaved abdominal skin of mice for 24 hours. The mice were then epicutaneously sensitized with 100 μl of 0.035% TNBS (w/v) in PBS, pH 5.5.

For pretreatment plus co-administration, mice were first pretreated for 24 hours as above. Thereafter, 6000 μg of UCA (100 μl of 6% solution, 60 mg/ml in PBS pH 5.5) were placed in the Hilltop chamber along with 35 μg of TNBS.

The results of this experiment are shown in Table III, below.

TABLE III cis-UROCANIC ACID INHIBITS CONTACT SENSITIVITY:
(PRETREATMENT VS PRETREATMENT
PLUS CO-ADMINISTRATION)

| TREATMENT | EAR THICKNESS (mm × $10^3$) | EAR SWELLING (mm × $10^3$) | % SUPPRESSION |
|---|---|---|---|
| NONE (PBS, pH 5.5) | | | |
| 24 Hours | 20.8 ± 2.1 | — | — |
| 48 Hours | 15.8 ± 3.6 | — | — |
| TNBS ONLY (35 μG) | | | |
| 24 Hours | 82.3 ± 7.0 | 61.5 | — |
| 48 Hours | 58.3 ± 10.0 | 42.5 | — |
| cis-UROCANIC ACID (PBS, pH 5.5) (PRE ONLY) plus TNBS (35 μG) | | | |
| 24 Hours | 40.3 | 19.5 | 68.3 |
| 48 Hours | 25.5 | 9.7 | 77.2 |
| cis-UROCANIC ACID (PBS, pH 5.5) (PRE + CO-AD) plus TNBS (35 μg) | | | |
| 24 Hours | 49.8 | 29.0 | 52.8 |
| 48 Hours | 34.6 | 18.8 | 55.8 |

Thus, pretreatment with cis-UCA before sensitization by TNBS resulted in a 68% and a 77% suppression of the 24 hour and 48 hour ear swelling response, respectively, to challenge with the cross-reacting hapten, TNCB.

In the pretreatment plus co-administration protocol, there was a 53% and a 56% suppression of the 24 hr and 48 hr ear swelling response, respectively, to challenge with TNCB.

D. cis-Urocanic Acid Inhibition of Contact Sensitivity is Dose Dependent

A dose-response study of the cis-UCA suppression of the contact sensitivity reactions was performed. The results of these experiments are shown in Table IV below.

TABLE IV cis-UROCANIC ACID INHIBITS CONTACT SENSITIVITY:
DOSE RESPONSE EFFECT

| TREATMENT | EAR THICKNESS (mm × $10^3$) | EAR SWELLING (mm × $10^3$) | % SUPPRESSION |
|---|---|---|---|
| NONE (PBS) | 19.3 ± 6.4 | — | — |
| TNBS ONLY (3.5 mg) | 162.3 ± 21.8 | 140.2 | — |
| TNBS + | | | |
| cis-UCA 200 μg | 109.0 ± 8.6 | 89.7 | 36.0 |
| cis-UCA 600 μg | 71.3 ± 16.2 | 52.0 | 63.0 | cis-UCA was dissolved in PBS, pH 7.2; ear thickness was measured 24 hours after challenge; N = 5

Thus, prior application of either 200 μg or 600 μg of cis-UCA 24 hours before induction of contact sensitivity by 3.5 mg TNBS resulted in a corresponding 36% or 63% suppression of ear swelling response. These results show that cis-UCA effectively suppresses the induction of contact sensitivity response in a controlled and dose-dependent fashion.

E. Alternative Routes of Administration of cis-UCA

The above results show that it should be possible to fabricate a controlled release device or a transdermal device that could deliver through intact skin a formulation consisting of either cis-UCA alone, or cis-UCA in combination with a sensitizing drug. In addition to this route of delivery, the efficacy of intradermal injection of cis-UCA prior to the epicutaneous application of the sensitizing agent was tested.

The results of these experiments are shown in Table V, below.

TABLE V

INTRADERMAL INJECTION OF cis-UROCANIC ACID INHIBITS
CONTACT SENSITIVITY

| TREATMENT | EAR THICKNESS (mm × $10^3$) | EAR SWELLING (mm × $10^3$) | % SUPPRESSION |
|---|---|---|---|
| NONE (PBS, pH 5–6) | | | |
| 24 Hours | 12.4 ± 3.7 | — | — |
| 48 Hours | 4.0 ± 1.7 | — | — |
| TNBS (35 μG) | | | |
| 24 Hours | 83.0 ± 7.9 | 70.6 | — |
| 48 Hours | 47.6 ± 4.9 | 43.6 | — |
| cis-UCA (200 μG) + TNBS (35 μG) | | | |
| 24 Hours | 48.8 ± 4.2 | 36.4 | 48.4 |
| 48 Hours | 33.8 ± 5.4 | 29.8 | 31.6 |

Thus, prior intradermal injection of 200 μg of cis-UCA 24 hours before induction of contact sensitivity by TNBS (35 μg) resulted in 48% and 32% suppression of the ear swelling response to epicutaneous challenge with 20 μl of 1% TNCB.

EXAMPLE 4

Inhibition of Contact Sensitization by the Mast Cell Degranulating Agent, Chloroouine The present inventors conceived that cis-UCA is a member of new class of counter-sensitizers that suppress contact sensitization by a mechanism involving the degranulation of cutaneous mast cells. As shown above, cis-UCA was highly effective in suppressing contact sensitization by a highly reactive chemical antigen, TNBS. Other experiments indicated that trans-UCA had much less suppressive activity. This difference was considered to reflect the unappreciated fact, for which supportive evidence is available, that cis-UCA is a potent mast cell degranulating agent, while trans-UCA is not.

According to the present invention, therefore, a correlation exists between the ability of an agent to suppress induction of contact sensitivity and its ability to induce mast cell degranulation. The present inventors therefore predicted that other mast cell degranulating agents would also suppress the induction phase of contact sensitization. This prediction was tested by examining the activity of chloroquine. Chloroquine is a well-known antimalarial drug and also acts a mast cell degranulating agent (Green, et al., *Skin Pharmacol.* 2:77–85 (1989)).

Sensitization with TNBS was induced as described above. Chloroquine (200 μg) was injected intradermally into five mice 24 hours before epicutaneous sensitization with TNBS.

The results of this experiment are shown in Table VI, below.

TABLE VI

CHLOROQUINE INHIBITION OF CONTACT SENSITIVITY

| TREATMENT | EAR THICKNESS (mm × $10^3$) | EAR SWELLING (mm × $10^3$) | % SUPPRESSION |
|---|---|---|---|
| NONE (PBS) | | | |
| 24 Hours | 16.8 ± 2.9 | — | — |
| 48 Hours | 16.8 ± 0.9 | — | — |
| TNBS ONLY (2.45 mG) | | | |
| 24 Hours | 100.6 ± 15.6 | 83.6 | — |
| 48 Hours | 160.8 ± 28.1 | 144 | — |
| TNBS + CHLOROQUINE (200 μG) | | | |
| 24 Hours | 67.4 | 50.6 | 39.6 |
| 48 Hours | 93.8 | 77.0 | 46.5 |

The chloroquine dose, 10% of the LD, was administered intradermally

Thus, intradermal injection of mice with a sublethal dose of chloroquine (10% of the $LD_{50}$) suppressed contact sensitivity by 40–47%.

EXAMPLE 5

A Mast Cell Membrane Stabilizing Agent Promotes Contact Sensitization

In view of the present inventors conception that mast cell degranulating agents act as counter-sensitizers, they further predicted that an agent which stabilizes mast cell membranes would not suppress, and might even enhance contact sensitization.

To test this prediction, sodium cromolyn, which is known to stabilize mast cell membranes (Klein et al., *Proc. Natl. Acad. Sci. USA* 86:8972–8976 (1989)), was tested in the same experiment in which chloroquine was tested above. The results are shown in Table VII, below.

TABLE VII

EFFECT OF CROMOLYN ON CONTACT SENSITIVITY

| TREATMENT | EAR THICKNESS (mm × $10^3$) | EAR SWELLING (mm × $10^3$) | % SUPPRESSION |
|---|---|---|---|
| NONE (PBS) | | | |
| 24 Hours | 16.8 ± 2.9 | — | — |
| 48 Hours | 16.8 ± 0.9 | — | — |
| TNBS (2.45 mG) | | | |
| 24 Hours | 100.6 ± 15.6 | 83.6 | — |
| 48 Hours | 160.8 ± 28.1 | 144 | — |
| TNBS plus CROMOLYN (20 μG) | | | |
| 24 Hours | 112.4 ± 11.8 | 95.6 | +14.1 |
| 48 Hours | 185.2 ± 16.1 | 168.4 | +17.0 |

Cromolyn was injected intradermally.

The results indicate that intradermal injection of sodium cromolyn (20 μg) failed to suppress contact sensitization. Rather, the effect of sodium cromolyn was to produce an enhancement of 14–17% in the contact sensitivity response. Other mast cell membrane stabilizing agents which are expected to have similar effects of sodium cromolyn include cyclosporin A, FK506, and corticosteroids.

EXAMPLE 6

Anti-Inflammatory Effect of Cis-Uca in the Skin

A male subject aged 54 years was stung by a bee on the medial aspect of the lower portion of the right leg. Within one hour the skin site surrounding the bite became inflamed and an allergic reaction of the delayed hypersensitivity type was seen 24 hours later. The skin area showed erythema, induration and was hot to the touch, classic inflammatory symptoms. This response persisted for several days.

The affected area was treated by application of 2% cis-UCA in a gel formulation (hydroxylpropylmethyl cellulose) to a 2–3 cm² area of inflamed skin. For a control, a similarly sized area of inflamed skin received the same hydroxylpropylmethyl cellulose gel without cis-UCA. Both treated areas were covered with a transparent dressing.

Approximately 1 hour later, it was observed that the erythema and induration disappeared from inflamed skin treated with cis-UCA. The inflamed site treated with the control gel showed no change.

This reversal of the inflammatory state was observed for the following 6 hours, and persisted into the next morning, 12 hours after application. The transparent dressings were removed 14 hours after initiation of treatment. The control skin site was observed to be indurated and red, while the cis-UCA-treated skin site was depressed (appearing normal) and lacked any red color, relative the surrounding inflamed skin.

It was concluded that cis-UCA acted to reduce an existing inflammatory skin reaction and is therefore useful as an anti-inflammatory agent. Preferably, pharmaceutically acceptable vehicles containing from about 0.1 to about 10% of cis-UCA or a derivative thereof, are suitable for this use.

EXAMPLE 7

Formulation of Transdermal Patches Containing a Counter-Sentizing Agent

A. cis-UCA-Containing Patch Which Counteracts Sensitizing Effect of the Drug Clemastine Two plastisol formulations containing the antihistamine clemastine will prepared as described below. Table VIII, below shows the formulations.

TABLE VIII

| Component | Clemastine Formulations (in parts) | |
|---|---|---|
| | 1 | 2 |
| PVC Resin | 59 | 58 |
| Dioctyl Phthalate | 37 | 36 |
| Clemastine (Drug) | 4 | 4 |
| cis-UCA | 0 | 2 |

Patches are prepared by mixing all the ingredients together and coating 5 ml thick deposits of this thick liquid onto a release lever. The coatings are then cured for 30 seconds at 300° F. to form 5 ml thick solid matrix patches.

In vitro tests of permeation of clemastine in the two formulations through human skin show that both formulations permeate similarly.

When the above formulations are applied to the skin of a human subject over a 24 hour period, Formulation 1 results in substantially more irritation and/or sensitization than does Formulation 2.

B. cis-UCA-Containing Patch Which Counteracts Sensitizing Effect of the Permeation Enhancer, Oleic Acid Three plastisol formulations containing the drug isosorbide dinitrate (ISDN) and the skin permeation enhancer oleic acid will be prepared esssentially as above for the clemastine patches. The formulations are summarized in Table IX, below.

TABLE IX

| Component | ISDN/Oleic Acid Formulation (in parts) Formulation | | |
|---|---|---|---|
| | 1 | 2 | 3 |
| PVC Resin | 55 | 51 | 50 |
| Dioctyl Phthalate | 35 | 31 | 30 |
| ISDN (Drug) | 10 | 10 | 10 |
| Oleic Acid (Enhancer) | 0 | 2 | 2 |
| cis-UCA | 0 | 0 | 2 |

When permeation rates are measured through human skin in vitro, it is found that the presence of oleic acid significantly enhances the permeation rate of ISDN.

All three patches are placed on the skin of human subjects over a 24 hour period. Patch 1, lacking oleic acid, and Patch 3, containing both oleic acid and cis-UCA show minimal irritation and/or sensitization. In contrast, Patch 2, containing oleic acid but no counter-sensitizing agent, induces substantial irritation and/or sensitization.

EXAMPLE 8

Purification and Concentration of Cis-Urocanic Acid

A. Purification of Cis-Urocanic Acid

A solution of photoisomerized trans-UA (ratio over 70:30 cis- to trans-; prepared as described in Example 1) was loaded to an ion exchange chromatographic column packed with Dowex 1-X8 (Biorad) and pre-equilibrated with 0.0125M ammonium acetate. After washing off unbound materials with 0.050M solution, cis-UCA and trans-UCA were eluted with a linear gradient of 4 L solution consisting of 0.050M ammonium acetate (2 L) and 0.5M of the same salt. Fractions containing cis-UA were identified using a UV-spectrophotometer and confirmed by HPLC. For scale preparation, 5 liters of photoisomerized solution of trans-UA was concentrated by lyophilization. The powder was dissolved in 1.25 L of 0.0125M ammonium acetate buffer, filtered, and applied to 600 ml packed gel. Fractions of 6 ml were collected on a Frac-200 fraction collector (Pharmacia) equipped with a peristaltic pump (P-1) and a 3-way flow diversion valve. Using this system, only fractions of interest were collected.

B. Concentration of the Urocanic Acid

Solutions of isomers or of cis-UA were concentrated in bulk form or in aliquots by lyophilization. For this purpose, the solutions were frozen in suitable containers in a freezing bath at −80° C. for 1.5 hours or in the Unitop chamber (Virtis) at −40° C. for 6 to 8 hours. Following the evacuation of the chambers, a primary and a secondary lyophilization cycle were used to remove solvent.

The primary cycle consisted of raising the temperature of the sample gradually from −40° C. to 15° C. for a period of 72 hours, and the secondary, and after the sample is dry, from 15° to 35° C. for a period of 48 hours. For a long term storage product, the chamber was filled with nitrogen gas and the vials stoppered using a mechanical stoppering device built in the unitop. The Teflon stoppers on each vial were secured using aluminum caps and a hand-held vial crimper device (Wheaton). Lyophilized samples were stored in the freezer and found to be stable for months under these conditions.

EXAMPLE 9

Suppression of Contact Hypersensitivity by Purified Cis-Urocanic Acid and the Induction of Immune Tolerance A. Immune Suppression of Balb/c Mice By Purified cis-Urocanic Acid The abdominal skin of Balb/c mice were shaved, and Finn chambers applied to a restricted area of the shaved skin 24 hours later. 0.2 ml of a Hydroxypropylmethyl cellulose (HPMC) gel containing various amounts of purified cis-urocanic acid (prepared as described in Example 8) were epicutaneously applied to the shaved skin site and the site covered by a Finn chamber. As a negative control, animals received 0.2 ml of hydroxypropylmethyl cellulose (HPMC) gel alone and the gel-treated site covered by a Finn chamber. The Finn chambers were firmly affixed by further application of an elastic bandage. One day later, the Finn chambers were removed and any excess gel gently wiped off with a moist tissue. Both experimental and control mice were sensitized by the single application of 10 $\mu$l of 1% DNCB in acetone to the skin area exposed to the gel, and contact hypersensitivity response elicited 5 days later by the topical application of 20 $\mu$l of 1% DNCB in acetone to the inner and outer surfaces of the right ear. Ear thickness measurements were made 24 and 48 hours post-challenge by a digital micrometer caliper.

B. Immune Tolerance Induction

To induce immune tolerance, Balb/c mice were treated with cis-UCA in gel formulation as outlined above and a sensitization response elicited in the standard manner. Two weeks later, the previously sensitized mice were re-sensitized by applying 10 $\mu$l of 1% DNCB to a second skin site on shaved backs of both control (non-sensitized) and experimental (immunosuppressed by prior treatment with cis-UCA) mice. Both control and experimental animals were challenged 5 days later by application of 20 $\mu$l of 1%

DNCB to the left ear; ear thickness measurements were made 24 hours later.

C. Results

1. Immune Suppression by Pretreatment With Purified cis-Urocanic Acid a. 24 Hour Pretreatment Regime For pretreatment, 100 µl of cis-UCA prepared in 2.5% HPMC gel (E4M PREM) dissolved in a 75% ethanol-25% water mixture or a 10% cis-UCA in HPMC gel were placed on a demarcated area of the shaved abdominal skin of 8 to 10 weeks old Balb/c strain of mice and the gel covered with a Finn chamber held in place by adhesive bandage. The chambers were removed 5 hours and 24 hours later, and the demarcated skin area painted with 10 µl of 1% DNCB in acetone. Challenge and measurement of elicitation were as described above.

Table X, below, present results of 24 hours pretreatment with a 1% cis-UCA and a 5% cis-UCA gel.

TABLE X cis-UROCANIC ACID INHIBITS CONTACT SENSITIVITY

| TREATMENT | EAR THICKNESS (mm × $10^3$) | EAR SWELLING (mm × $10^3$) | % SUPPRES-SION |
|---|---|---|---|
| NONE (HPMC GEL) | | | |
| 24 Hours | 244 ± 8 | — | — |
| 72 Hours | 241 ± 4 | — | — |
| DNCB ONLY (100 µG) | | | |
| 24 Hours | 332 ± 21 | 88.8 | — |
| 72 Hours | 313 ± 32 | 72.0 | — |
| cis-UROCANIC ACID 2 mg (1%) (HPMC GEL) (Petreat) + DNCB (100 µg) | | | |
| 24 Hours | 270 ± 16 | 26 | 71 |
| 72 Hours | 288 ± 23 | 48 | 33 |
| cis-UROCANIC ACID 10 mg (5%) (HPMC gel) (Petreat) + DNCB (100 µg) | | | |
| 24 Hours | 261 ± 15 | 18 | 80 |
| 72 Hours | 270 ± 15 | 30 | 59 |

For the 1% cis-UCA gel, 71% and 33% suppression of ear swelling response were observed 24-hours and 48-hours post-challenge, respectively. For a 5% cis-UCA gel, an 80% and 59% suppression of the ear swelling response were obtained at 24 hours and 48 hours, respectively.

b. Co-Delivery

In one experiment, a 5% cis-UCA gel was either co-delivered with 1% DNCB or delivered for 24 hours prior to sensitization with 1% DNCB. Sensitization was carried in the gel formulation for 24 hours. The results are seen in Table XI, below.

TABLE XI

COMPARISON OF THE CO-DELIVERY AND 24 HOURS PRETREATMENT ON IMMUNE SUPPRESSION BY CIS-UROCANIC ACID

| TREATMENT | EAR THICKNESS (mm × $10^3$) | EAR SWELLING (mm × $10^3$) | % SUPPRES-SION |
|---|---|---|---|
| NONE (HPMC GEL) n = 5 | | | |
| 24 Hours | 238 ± 9 | — | — |
| 48 Hours | 230 ± 9 | — | — |
| DNCB gel (100 µg) only n = 7 | | | |
| 24 Hours | 292 ± 13 | 55 | — |
| 48 Hours | 291 ± 20 | 60 | — |
| Co-Delivery (UCA 10 mg + DNCB 100 µg) n = 8 | | | |
| 24 Hours | 277 ± 27 | 39 | 28 |
| 48 Hours | 273 ± 23 | 43 | 29 |
| NONE (HPME gel) for 48 hours n = 5 | | | |
| 24 Hours | 230 ± 4 | — | — |
| 48 Hours | 251 ± 9 | — | — |
| 24 Hours Pretreat (UCA 10 mg) + DNCB (100 µg) n = 6 | | | |
| 24 Hours | 260 ± 19 | 29 | 52 |
| 48 Hours | 259 ± 12 | 20 | 69 |

The modest level of inhibition was observed at the 24-hour post-challenge measurement, which was not statistically significant. By contrast, animals pretreated for 24 hours showed significant inhibition of sensitization of 52% and 69% inhibition at 24-hours and 48-hours post-challenge, respectively.

c. 5 Hours Versus 24 Hours Pretreatment

In another experiment, using a 7.5% cis-UCA gel, the effect of 5 hour pretreatment was compared with 24 hour pretreatment regime. The 5-hour versus 24 hours pretreatment results are shown in Table XII, below.

TABLE XII

COMPARISON OF THE 5 HOURS VERSUS 24 HOURS PRETREATMENT ON IMMUNE SUPPRESSION BY CIS-UROCANIC ACID

| TREATMENT | EAR THICKNESS (mm × $10^3$) | EAR SWELLING (mm × $10^3$) | % SUPPRES-SION |
|---|---|---|---|
| NONE (HPMC GEL) n = 6 | | | |
| 24 Hours | 237 ± 8 | — | — |
| 48 Hours | 236 ± 15 | — | — |
| DNCB only (100 µg) for 5 hours Pretreat n = 8 | | | |
| 24 Hours | 320 ± 34 | 83 | — |
| 48 Hours | 299 ± 30 | 63 | — |
| DNCB only (100 µg) for 24 hours Pretreat n = 8 | | | |
| 24 Hours | 353 ± 30 | 116 | — |
| 48 Hours | 316 ± 33 | 80 | — |
| 5 Hours Pretreat (UCA 15 mg) + | | | |

TABLE XII-continued

COMPARISON OF THE 5 HOURS VERSUS 24 HOURS PRETREATMENT ON IMMUNE SUPPRESSION BY CIS-UROCANIC ACID

| TREATMENT | EAR THICKNESS (mm × $10^3$) | EAR SWELLING (mm × $10^3$) | % SUPPRES-SION |
|---|---|---|---|
| DNCB (100 μg) n = 8 | | | |
| 24 Hours | 285 ± 27 | 42 | 46 |
| 48 Hours | 284 ± 20 | 42 | 27 |
| 24 Hours Pretreat (UCA 15 mg) + DNCB (100 μg) n = 8 | | | |
| 24 Hours | 288 ± 25 | 47 | 59 |
| 48 Hours | 276 ± 14 | 36 | 54 |

A significant inhibition of 46% and 27% at 24-hours and 48-hours post-challenge, respectively was observed for the 5-hour pretreat regime. This compares favorably with the results obtained using the standard 24-hour pretreatment regime, which gave 59% and 54% inhibition for the 24-hour and 48-hour post-challenge, respectively.

2. Cis-Urocanic acid induces a state of immune tolerance

Balb/c mice (N=8) were pretreated for 24 hours with 1% cis-UCA in HPMC gel or 5% cis-UCA in HPMC gel on the shaved abdominal skin (site 1), and challenged on the right ear five days later. The cis-UCA-treated mice were immunosuppressed as shown in Table X. The same mice were re-sensitized with DNCB on a demarcated area of their shaved backs and re-challenged five days later on their left ears, and the ear thickness measured 24 hours post-challenge.

The results of this experiment are presented in Table XIII, below.

TABLE XIII

CIS-UROCANIC ACID INDUCES IMMUNE TOLERANCE

| TREATMENT | EAR THICKNESS (mm × $10^3$) | EAR SWELLING (mm × $10^3$) | % SUPPRESSION |
|---|---|---|---|
| NONE (HPMC GEL) (day -1) | | | |
| 24 Hours DNCB only (100 μG) (day 22) | 256 ± 5 | — | — |
| 24 Hours Cis-Urocanic Acid 2 mg (HPMC GEL) (day -1) + DNCB (100 μg) (day 22) | 401 ± 47 | 145 | — |
| 24 Hours Cis-Urocanic Acid 10 mg (HPMC gel) (day -1) + DNCB (100 μg) (day 22) | 327 ± 60 | 70 | 51 |
| 24 Hours | 334 ± 17 | 84 | 42 |

Thus, mice that received the 1% cis-UCA gel displayed 51% inhibition of the ear swelling response, while mice that received the 5% cis-UCA gel showed a 42% inhibition of the ear swelling response.

EXAMPLE 10 cis-Urocanic Acid Induces Mast Cell Degranulation

A. Chymase Depletion of Mast Cell by Cis-urocanic Acid

Figure 2:
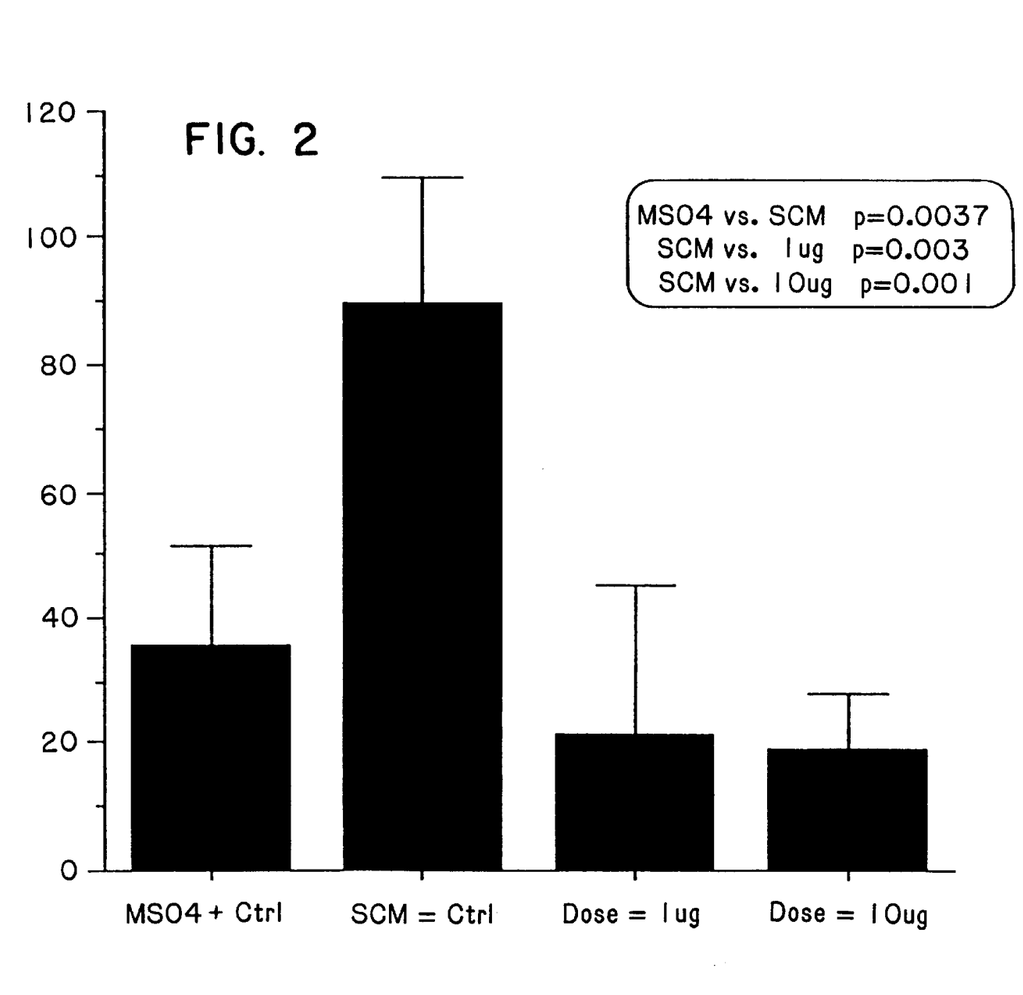
FIG. 2 is a graph illustrating Chymase Depletion from Mast Cells by Cis-Urocanic Acid.

Chymase is a proteolytic enzyme with chymotrypsin activity that is released from dermal mast cells upon degranulation. The enzyme has been implicated in proteolytic breakdown of endothelial cell basement membrane matrix proteins and to thereby facilitate leukocyte diapedesis. The release of chymase from mast cells was detected as a depletion of chymase-specific immunohistochemical staining observed in cryosections of the dermis in skin organ cultures. As a positive control 5 mM of morphine sulfate ($MSO_4$+ctrl) was added to the culture medium bathing the skin organ cultures. The negative control was untreated culture medium (SCM-ctrl). Cis-urocanic acid was added to the culture medium at 1 μg/ml and 10 μg/ml.

The results of these experiments are presented in FIG. 2.

Cryosections obtained from control untreated skin displayed 88±12 chymase positive mast cell per $mm^2$. The positive control treated with morphine sulfate were significantly depleted of chymase positive cells (37±15). Skin treated with either 1 μg/ml or 10 μg/ml were also significantly depleted of chymase positive mast cells, 22±20, and 20±10 chymase positive mast cells, respectively.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains.

What is claimed is:

1. A method for inducing immunological tolerance in a subject to a skin sensitizing drug or agent administered to the skin, which method comprises administering to said subject prior to, at the onset of, or both prior to and at the onset of, dermal or transdermal delivery of said sensitizing drug or agent, an effective amount of at least one mast cell degranulating agent.

2. A method according to claim 1, wherein said skin sensitizing drug or agent is a transdermally delivered therapeutic drug, a skin permeation enhancing substance, an excipient or a combination thereof.

3. A method according to claim 1, wherein said at least one mast cell degranulating agent is selected from the group consisting of cis-urocanic acid or an analogue or a metabolite thereof; chloroquine; capsaicin; morphine sulfate; a sodium channel ionophore; a calcium channel ionophore; an inhibitor of $Na^+/K^+$ channel ATPase; quinine; 4-aminopyridine; an anti-human IgE antibody; compound 48/80; substance P; estradiol; somatostatin; clonidine; progesterone; carbachol; and spantide.

4. A method according to claim 3 wherein said at least one mast cell degranulating agent is cis-urocanic acid, or an analogue or a metabolite thereof.

5. A method according to claim 4 wherein said cis-urocanic acid analogue is selected from the group consisting of a cis or trans isomer of 1-furanacrylic acid, a cis or trans isomer of 2-pyrrole acrylic acid, a cis or trans isomer of 2-thiopheneacrylic acid, and dihydrourocanic acid.

6. A method according to claim 4 wherein said cis-urocanic acid metabolite is selected from the group consisting of histamine, $N^1$-methylhistamine, $N^1$-methylhistidine, histidine, imidazolepyruvic acid, $N^3$-methylhistidine, imidazoleacetic acid, hydantoin 5-propionic acid, and imidazolonepropionic acid.

7. A method for preventing or inhibiting the skin irritating or skin sensitizing effect of a drug administered to the skin, which method comprises administering before, together with, before and together with, or after said drug, an effective amount of at least one mast cell degranulating agent.

8. A method for preventing or inhibiting the skin irritating or skin sensitizing effect of a component of a dermal or transdermal drug delivery system, which method comprises administering before, together with, before and together with, or after said component, an effective amount of at least one mast cell degranulating agent.

9. A method according to claim 8, wherein said component of the transdermal delivery system is a transdermally delivered therapeutic drug, a skin permeation enhancing substance, an excipient or a combination thereof.

10. A method according to claim 8, wherein said at least one mast cell degranulating agent is transdermally administered together with said component.

11. A method according to any one of claims 7–10, wherein said at least one mast cell degranulating agent is selected from the group consisting of cis-urocanic acid or an analogue or a metabolite thereof; chloroquine; capsaicin; morphine sulfate; a sodium channel ionophore; a calcium channel ionophore; an inhibitor of $Na^+/K^+$ channel ATPase; quinine; 4-aminopyridine; an anti-human IgE antibody; compound 48/80; substance P; estradiol; somatostatin; clonidine; progesterone; carbachol; and spantide.

12. A method according to claim 11, wherein said at least one mast cell degranulating agent is cis-urocanic acid, or an analogue or a metabolite thereof.

13. A method according to claim 12, wherein said cis-urocanic acid analogue is selected from the group consisting of a cis or trans isomer of 1-furanacrylic acid, a cis or trans isomer of 2-pyrrole acrylic acid, a cis or trans isomer of 2-thiopheneacrylic acid, and dihydrourocanic acid.

14. A method according to claim 12, wherein said cis-urocanic acid metabolite is selected from the group consisting of histamine, $N^1$-methylhistamine, $N^1$-methylhistidine, histidine, imidazolepyruvic acid, $N^3$-methylhistidine, imidazoleacetic acid, hydantoin 5-propionic acid, and imidazolonepropionic acid.

15. A method according to claim 1, 7 or 9, wherein said drug is selected from the group consisting of an angiotensin converting enzyme inhibitor; a beta adrenergic receptor blocker; an anti-hypertensive drug other than an angiotensin converting enzyme inhibitor or a beta adrenergic receptor blocker; an anti-histamine; an anti-asthmatic drug; a non-steroidal anti-inflammatory drug; a central nervous system active drug; a weight control drug; an anticoagulant; a potassium control drug; an immunomodulatory drug; and a decongestant.

16. A method according to claim 8, wherein said component is a skin permeation enhancing substance.

17. A method according to claim 16, wherein said skin permeation enhancing substance is selected from the group consisting of ethanol, oleic acid, oleyl alcohol, linoleic acid, propylene glycol, lauramidopropyl betaine, dimethylsulfoxide, dimethylformamide, decylmethylsulfoxide, N-methylpyrrolidone, isopropyl alcohol, t-butanol and sodium lauryl sulfate.

18. An article useful for preventing or inhibiting the skin irritating or skin sensitizing effect of a component of a dermal or transdermal drug delivery system, said article comprising:

(a) a dermal or transdermal delivery system comprising a therapeutic drug of interest; and (b) an effective amount of at least one mast cell degranulating agent.

19. An article according to claim 18, wherein said mast cell degranulating agent is included in the transdermal delivery system (a).

20. An article according to claim 18 wherein said at least one mast cell degranulating agent is selected from the group consisting of cis-urocanic acid or an analogue or a metabolite thereof; chloroquine; capsaicin; morphine sulfate; a sodium channel ionophore; a calcium channel ionophore; an inhibitor of $Na^+/K^+$ channel ATPase; quinine; 4-aminopyridine; an anti-human IgE antibody; compound 48/80; substance P; estradiol; somatostatin; clonidine; progesterone; carbachol; and spantide.

21. An article according to claim 20 wherein said at least one mast cell degranulating agent is cis-urocanic acid, or an analogue or a metabolite thereof.

22. An article according to claim 18, wherein said drug of interest is selected from the group consisting of an angiotensin converting enzyme inhibitor; a beta adrenergic receptor blocker; an anti-hypertensive drug other than an angiotensin converting enzyme inhibitor or a beta adrenergic receptor blocker; an anti-histamine; an anti-asthmatic drug; a non-steroidal anti-inflammatory drug; a central nervous system active drug; a weight control drug; an anticoagulant; a potassium control drug; and a decongestant.

23. An article according to claim 18, wherein the transdermal delivery system (a) further comprises a skin permeation enhancing substance.

24. An article according to claim 23, wherein said skin permeation enhancing substance is selected from the group consisting of ethanol, oleic acid, oleyl alcohol, linoleic acid, propylene glycol, lauramidopropyl betaine, dimethylsulfoxide, dimethylformamide, decylmethylsulfoxide, N-methylpyrrolidone, isopropyl alcohol, t-butanol, and sodium lauryl sulfate.

25. A pharmaceutical composition useful for preventing or inhibiting the skin irritating or skin sensitizing effect of a component of a dermal or transdermal drug delivery system, said composition comprising:

an amount of at least one mast cell degranulating agent effective to prevent or inhibit the skin irritating or skin sensitizing effect of a component of a dermal or transdermal drug delivery system and an acceptable pharmaceutical carrier.

26. A pharmaceutical composition according to claim 25, wherein said at least one mast cell degranulating agent is cis-urocanic acid, or an analogue or a metabolite thereof.

27. A pharmaceutical composition according to claim 26, wherein the cis-urocanic acid analogue is selected from the group consisting of a cis or trans isomer of 1-furanacrylic acid, a cis or trans isomer of 2-pyrrole acrylic acid, a cis or trans isomer of 2-thiopheneacrylic acid, and dihydrourocanic acid.

28. A pharmaceutical composition according to claim 26, wherein the cis-urocanic acid metabolite is selected from the group consisting of histamine, $N^1$-methylhistamine, $N^1$-methylhistidine, histidine, imidazolepyruvic acid, $N^2$-methylhistidine, imidazoleacetic acid, hydantoin 5-propionic acid, and imidazolonepropionic acid.

29. A pharmaceutical composition according to claim 25, wherein the said at least one mast cell degranulating agent is in a form for dermal or transdermal administration.

30. A method for inhibiting an inflammatory reaction in the skin of a subject associated with a skin sensitizing reaction, which method comprises administering to said subject an effective amount of at least one mast cell degranulating agent.

31. A method according to claim 30, wherein said at least one mast cell degranulating agent is selected from the group consisting of cis-urocanic acid or an analogue or a metabolite thereof; chloroquine; capsaicin; morphine sulfate; a sodium channel ionophore; a calcium channel ionophore; an inhibitor of $Na^+/K^+$ channel ATPase; quinine; 4-aminopyridine; an anti-human IgE antibody; compound 48/80; substance P; estradiol; somatostatin; clonidine; progesterone; carbachol; and spantide.

* * * * *